United States Patent [19]

Wenke

[11] Patent Number: 5,100,436
[45] Date of Patent: Mar. 31, 1992

[54] OXIDATIVE HAIR DYEING PROCESS WITH CATALYTIC PRETREATMENT

[75] Inventor: Gottfried Wenke, Woodridge, Conn.

[73] Assignee: Clairol Incorporated, Stamford, Conn.

[21] Appl. No.: 666,108

[22] Filed: Mar. 7, 1991

[51] Int. Cl.$^5$ .............................................. A61K 7/13
[52] U.S. Cl. .......................................... 8/405; 8/406; 8/408; 8/410; 8/428; 8/429; 424/70
[58] Field of Search .................. 8/405, 406, 428, 429, 8/408, 410; 424/70; 132/38

[56] References Cited

U.S. PATENT DOCUMENTS

| | | | |
|---|---|---|---|
| 3,948,596 | 4/1976 | Kolopissis et al. | 8/408 |
| 3,950,532 | 4/1976 | Bouillon et al. | 8/405 |
| 3,981,676 | 9/1976 | Ghilardi et al. | 8/421 |
| 3,989,447 | 11/1976 | Kolopissis et al. | 8/408 |

FOREIGN PATENT DOCUMENTS 1463870 11/1966 France .

*Primary Examiner*—Paul Lieberman
*Assistant Examiner*—William S. Parks
*Attorney, Agent, or Firm*—Charles J. Zeller

[57] ABSTRACT

In a method for oxidatively dyeing hair, a pretreatment which comprises contacting hair with an aqueous solution of an effective amount of particular metal/chelate complexes followed by treatment with oxidative dye mixtures is disclosed. The process serves to conform the oxidative dyeing rate of virgin hair to that of the normally noncongruent rate of nonvirgin hair, so as to enhance the efficiency of the oxidative dyeing process, without reducing the intensity or variety of color available.

12 Claims, No Drawings

OXIDATIVE HAIR DYEING PROCESS WITH CATALYTIC PRETREATMENT

BACKGROUND OF THE INVENTION

1. Field of the Invention

The present invention relates to oxidative hair dyeing processes, and particularly to a novel and unexpected method for conforming the oxidative dyeing rate of virgin hair to that of non-virgin hair, resulting in substantial improvements to the efficiency of the process.

2. Background of the Prior Art

Oxidative hair dyeing processes are generally distinguished from other hair dyeing processes, by virtue of an essentially in-fiber synthesis of color species generated from a three component reactive composition. The three reactive components contained in an oxidative hair dyeing composition are as follows:

(1) The primary dye intermediates,
(2) The color couplers or modifiers, these components 1 and 2 being commonly referred to as dye precursors, and
(3) The oxidizers.

Hair dyed using this process retains its color until the color is chemically removed by bleaching or other processes. The process is thus deemed to be a permanent dyeing process.

Generally, the process is conducted at alkaline pH 9 to 10, requires 20 to 40 minutes, and usually employs hydrogen peroxide as the oxidizer.

Oxidative damage to hair, after a single dye application, from such compositions, may be small. However, when these dye applications are repeated, or when combined with other cosmetic treatments such as permanent waving, relaxing, or extensive bleaching, the hair damage is considerably more severe. Such damage is normally experienced by the consumer in the form of coarse feel to the hair and tendency of the hair to break-off.

Consumers generally have their hair dyed periodically, typically once a month, sometimes as often as twice a month. Between each hair dyeing session, new hair grows out from the scalp. Thus, it is seen that typically the hair to be dyed comprises virgin hair (proximate the scalp) and previously dyed hair (proximate the virgin hair). Moreover, the previously dyed hair may comprise hair that has undergone any number of discrete permanent dyeing treatments, depending on its length and frequency of dyeing treatments. Although hair dyeing treatments are those most often involved, the nonvirgin hair may have been also subjected to any of the other chemical treatments, such as permanent waving, enumerated above.

It is well known that when hair is treated with peroxide or other oxidizers, an essential amino-acid called cystine, which is found in hair, undergoes oxidation to cysteic acid. This chemical reaction leads to a weakening of the hair structure, making the hair dryer and prone to breakage. Accordingly, there is reason for consumers to believe that exposure to hydrogen peroxide during the oxidative dyeing of hair is a primary causative factor responsible for the damage to hair.

The hair coloring industry has attempted to satisfy this consumer concern by reformulating oxidative hair dyes with metal ion catalyst that hastens the peroxide oxidation reaction of the dye precursors and thus reduce the amount of time hair is exposed to the damaging effects of hydrogen peroxide or other oxidizers.

However, these catalytic oxidative dyeing processes have met with little or no commercial success for several reasons. First, it is well known that molecular diffusion of dye materials into nonvirgin hair or cosmetically treated hair, occurs faster than diffusion into virgin hair. Accordingly, the presence of catalyst, which hasten the oxidative dyeing process, itself serves to further disproportionate the uneven rate of dyeing of the new hair growth as compared to that of previously treated hair. Secondly, the nonvirgin or previously treated hair has a greater affinity for the metal catalyst ion than does virgin or new hair. Thus, there is a greater amount of the metal ion catalyst deposited on the nonvirgin hair, where the molecular diffusion of the dye materials also takes place more rapidly. This serves only to aggravate the uneven or disproportionate dyeing of the two types of hair.

These disproportionate dyeing rates have in the past necessitated the use of metal ion catalyst concentrations that are high enough to provide a sufficiently deep shade of color in the virgin hair so that the faster accumulation of color in the nonvirgin hair is less perceivable. Thus, an excessive accumulation of metal ions necessarily takes place. Such high metal ion concentrations on the hair, when in contact with alkaline peroxide, can cause exothermic reactions to take place which lead to severe discomfort and damage. Higher metal ion concentrations also inherently create a coarse hair feel. Therefore, despite the shorter treatment time made possible from the metal ion catalyst, no noticeable decrease in hair damage is apparent to the consumer.

Patents issued which are exemplary of these prior art drawbacks are set forth below. German Patent DE 2,028,818 to the Gillette Company discloses an oxidative dyeing process for hair wherein the hair is pretreated with a solution of metal salt at concentrations of from about 0.01 to 0.15 Molar for 5 minutes. The hair is then rinsed with water and exposed to a solution containing dye precursors and hydrogen peroxide at alkaline pH of about 9.5 for 5 minutes. This dyeing time is significantly shorter than the time for conventional oxidative dyeing processes. However, the required concentration of metal ions to sufficiently catalyze acceptable levels of dyeing in virgin hair was so high that tensile strength measurements of the hair have indicated no noticeable decrease in hair damage as compared to the conventional processes, notwithstanding the acceleration of the oxidative reaction. The attendant risk of perceivable uneven dyeing, absent severe metal build-up and damage, leaves this process of little commercial value.

International patent WO88/01162 to Goldwell discloses a procedure for low pH dyeing wherein metal salt catalysts are added directly to a cream or gel-like oxidative dye mixture, rather than applying the catalyst separately to hair as a pretreatment. Because low metal concentrations were employed, the Goldwell process is suitable solely for treating nonvirgin (or previously cosmetically treated) hair to temporarily tint or tone the hair. The Goldwell process cannot completely dye virgin, i.e., chemically unaltered, hair to obtain a permanent and intense color.

A method for oxidatively dyeing hair in a rapid but permanent fashion, which changes the chemistry of this reaction on hair, and particularly which could conform the rate of oxidatively dyeing virgin hair to approximate that of the faster nonvirgin hair rate, while substantially reducing metal accumulation, would represent an unexpected advancement in the art and would satisfy a long felt need in the industry.

SUMMARY OF THE INVENTION

According to the present invention there is provided, in contrast to the prior art where aqueous solutions of transition metal ions catalyze the oxidative dyeing of virgin hair at a substantially disproportionate rate to that of nonvirgin hair, an unexpectedly superior process which conforms the nonvirgin and virgin hair dyeing rates. The process of the present invention involves using an effective amount of transition metal ions complexed with dipyridyl or o-phenanthroline chelating agents as an aqueous pretreatment to hair prior to the subsequent application of an oxidative dyeing mixture.

The use of metal chelating agents generally in the dyeing of fibers, other than hair, is not new. Early attempts to use metal chelate complexes in the dyeing of fibers were adapted from the textile industry, and like most textile dyeing techniques they have met with little success when coloring human hair.

For example, as early as 1936, Mr. Siegfried Peterson disclosed in U.S. Pat. No. 2,190,848 using metal chelating agents such as dipyridyl and o-phenanthroline, as well as others, in an aqueous post-treatment of cellulosic textile fibers after they had already been colored. The treatment aided in light and water fastness. The coloring was by a direct dye process as distinguished from oxidative dyeing.

The so-called "metal chelate dyeing process for hair" developed by Goldemberg is disclosed in U.S. Pat. No. 3,075,821. In Goldemberg, metal ion salt compositions are used as mordants, to fix, a minute but color producing, "post-treatment" amount of organic chelating agents, comprising dithio-oxamides, which could also contain pyridyl constituents. The reaction of the dithio-oxamide constituent and the metal-ions was directly responsible for coloring the hair as distinguished from catalyzing other reactions that color the hair.

An alternative "metal chelate dyeing process" has been to color the hair with an aqueous solution containing both a metal salt and a chelating agent in complexed form, with adjustment of the pH from 10 to about 11 in order to fix the color directly in the hair. In U.S. Pat. No. 3,429,646 M. W. Steed discloses using color producing amounts of chelating agents such as dipyridyl and o-phenanthroline.

These processes of Goldemberg and Steed require particular metal ions and the appropriate complexes in sufficient concentration to produce color. Steed warns that the copper I complex of dipyridyl, Cu(dipyridyl)$_2$+, is oxidizable to the copper II dipyridyl complex, even by a weak oxidizer such as the oxygen present in the air. This is a problem in the Steed process because the strongly colored Cu I complex could be oxidized by air to form the weakly colored Cu II complex. Accordingly, the presence of strong oxidizing agents such as hydrogen peroxide are avoided in the Steed process to prevent oxidation of the highly colored Cu I complex.

Inasmuch as the Cu II complexes and other non-coloring materials employed in the present invention catalyze the oxidative dye reactions, rather than dye hair directly, their effective non-coloring use in the presence of, and their compatibility with, oxidizing agents, is novel and unexpected.

More recently, metal chelates have been employed in, for example, Japanese Publication No. Sho 45/1970-24,478 to form chelated copper complexes of, for example, dimethyl glyoxime (diglyme). The chelates were intimately mixed into, easily oxidized auto oxidative, dye mixtures, which excluded oxidants such as peroxide. Substantial amounts of these metal complexes were present and generated the color during air oxidation.

Thus, it can be seen that a principal distinction of the present invention, over all prior proposals for dyeing with metal chelating complexes, is that the present invention calls for non-color developing amounts of metal chelate complexes, used as pretreatment catalyst, rather than as direct dyes. Surprisingly, as catalyst, they conform the disproportional oxidative dye rates of virgin and nonvirgin hair.

Moreover, the inherent damage to hair from excessive metal accumulation and from oxidation of cystine which normally occur during metal ion catalytic dyeing are substantially inhibited. It may therefore be seen that a principal object of the present invention is to provide a new and unexpected method for oxidatively dyeing hair, which conforms the dyeing rates of virgin and nonvirgin hair.

It is a further object of the invention to provide a new and unexpected method for catalyzing the oxidative dyeing process with substantially lower concentrations of metal.

It is an additional object of the present invention to provide a new and improved method for using metal chelates in the dyeing of hair.

It is a still further principal object of the present invention to provide a new and improved method for oxidatively dyeing hair by reducing not only the exposure time to hydrogen peroxide, but also by moderating the harsh character of the peroxide oxidation.

With the foregoing and other objects in mind, this invention will now be particularly described, and other objects and advantages thereof will be either implicitly or explicitly apparent from the following description, examples and appended claims.

DETAILED DESCRIPTION AND PREFERRED EMBODIMENTS

In setting forth the present invention, it will be understood that certain of the transition metal complexes hereinafter described, for example, copper II complexes of 2,2'-dipyridyl or o-phenanthroline, inherently possess certain coloring qualities in water solution. However, the techniques and compositions of the present invention are distinguishable from such coloring propensities, because the metal chelate complexes of the present invention are employed in amounts substantially below that required to bring about direct coloring in human hair.

As used herein, "virgin hair" refers to hair that has not been chemically altered by any chemical treatment such as oxidative hair dyeing, permanent waving, straightening or relaxing, bleaching and the like, but includes hair that has been weathered by the environment, shampooed, conditioned or dyed by temporary or semipermanent hair dyes. "Nonvirgin hair" or "treated hair" refers to hair that has been chemically altered by one or more of the aforementioned chemical treatments.

In accordance with the present invention, a novel coloring effect occurs during oxidative dyeing reactions, particularly with hydrogen peroxide The metal ion/chelate complexes of the present invention serve to catalytically rather than directly participate in those hair coloring reactions.

In the process of the present invention, an aqueous pretreatment solution of a transition metal salt that has been complexed with a chelating agent selected from the group consisting of 2,2'-dipyridyl or o-phenanthroline is applied to a head of hair in which both virgin and treated hair is present. The pretreatment solution is retained in contact with the hair for a time sufficient for the complex to be deposited on the virgin and treated hair portions Contact time on the hair is for about 1 to about 15 minutes, preferably for about 5 to 15 minutes. The hair is then rinsed to remove excess complex. Thereafter, an oxidative dye mixture of dye intermediates, couplers and oxidizer is applied to the hair in conventional manner for a period of from about 5 to about 30 minutes, preferably from about 5 to 15 minutes. It is an important aspect of the present invention that the nature of the hair does not appreciably materially influence the affinity the hair has for the transition metal ion complex. Moreover, it is a surprising and unexpected outcome of the pretreatment that a sufficient concentration of the complex can be deposited on both virgin and treated hair to essentially uniformly accelerate the oxidation of the hair dye precursors. This is especially the case in view of the very low concentrations of the complex present in the pretreatment solution, as hereinafter set forth.

The metal ions present in the pretreatment solution may be provided in the form of transition metal such as copper, cobalt, iron, manganese. Particularly effective results have been obtained with copper II and the cupric form is accordingly preferred.

The metal ions may be provided from any water soluble salt including for example sulfates, nitrates, phosphates, acetates, chlorides, and citrates of the above enumerated metals.

The pretreatment solution may be prepared by simply forming an aqueous solution of a previously prepared complex. Alternatively, the pretreatment solution may be prepared by admixing an aqueous solution of the transition metal salt with an alcoholic solution of the 2,2'-dipyridyl or o-phenanthroline chelating agent. Preferably, the chelating agent is in an equal molar amount equivalent to the weight of the metal ions present in the pretreatment solution. The pretreatment solution has a pH of from about 6 to about 10, preferably between about 8 to about 9, which may be obtained with a suitable amount of pH adjusting agent, for example, citric acid, sodium hydroxide and the like. Any cosmetically acceptable low molecular weight alcohol such as ethanol or isopropanol may be used to prepare the alcoholic solution of the chelating agent. The pretreatment solution preferably contains one or more other constituents to enhance its suitability for application to hair. For example, the pretreatment solution is conveniently formulated as a shampoo which contains sufficient amounts of surfactants, thickeners, and other conventional shampoo ingredients to permit its application to hair as a somewhat viscous liquid which ensures that it does not run down from the head of the consumer.

The amount of the metal ion complex present in the pretreatment solution should be a minimum catalytic amount and less than the amount needed for inherent color development from the metal ion complex itself. It should be realized, however, that not all of the metal ion complexes will be a colored complex. Thus, the copper II-dipyridyl is not colored appreciably. The amount of the complex may range from about 0.001 to 0.1%, preferably from about 0.005 to about 0.05%, most preferably from about 0.005 to 0.01%, by weight of pretreatment solution when the pretreatment solution is in the preferred form of a flowable but somewhat viscous liquid such as a shampoo, the concentration of the complex therein is preferably toward the higher end of this range, typically from about 0.01 to about 0.05% by weight of the pretreatment solution. By way of contrast, the amount of copper salt which would be need to catalyze the Gillette process would be from 0.16% to 2.4% by weight of pretreatment solution.

The acceleration of the reaction rate is a function of the amount of metal ion complex deposited onto the hair from the pretreatment solution. A catalytically effective amount of complex is deposited on the hair. By "catalytically effective amount" is meant an amount which will upon deposition accelerate the hair dyeing reactions to enable the completion of the oxidative dyeing reactions within the 30 minute period previously mentioned, and without causing undue discomfort or skin irritation to the user. For the copper II-dipyridyl complex, this amount of the copper II deposited on the hair is generally in the range of from about 100 to about 1000 ppm, irrespective of the type of hair, preferably from about 200 to about 700 ppm. Below the minimum amount, too little of the complex is deposited to provide sufficient catalysis for the oxidative reactions. Above the upper value, the oxidative reactions will progress more rapidly, with possible release of sufficient heat to cause skin irritation. However, amounts above the upper value are not needed inasmuch as the color development is wholly satisfactory below that value. For other transition metal complexes, the amounts of the complex deposited on the hair may vary somewhat, depending upon the catalytic efficacy of the complex relative to the copper II complex.

As previously indicated, the pH of the pretreatment solution is between 6 and about 10, preferably from about 7.5 to 9. Advantageously, when dyeing hair from a lighter to a darker shade, the subsequent dyeing with the dye precursors can take place at a pH range close to neutral, typically from about 6 to about 8.5. This is far less harmful to hair than pH's of from 9 to 10, which are required with conventional oxidative hair dyeing processes. Where the hair must first be lightened, that is, when dyeing dark hair to a lighter shade, the pH of the hair dyeing precursors must be in the 9 to 10 range, notwithstanding the use of the pretreatment solution.

As described earlier, the pretreatment step of the present invention is preferably maintained in contact with the hair for from 5 to 10 minutes, after which the hair is rinsed with water and the oxidative dyeing mixture is applied.

The oxidative dyeing mixture comprises conventional primary dye intermediates, color couplers, and oxidizers.

Any of the conventional dyes and coupling agents use with ordinary oxidant compositions for hair coloring can be employed in the compositions of this invention to achieve a wide variety of tints and hues. Typically useful primary intermediates and couplers are mentioned, for example in U.S. Pat. Nos. 3,536,436; 4,092,102; 3,884,627; 3,981,677 and British Patent 2,205,329, incorporated by reference herein, and include para-phenylene diamines; para-aminophenols; ortho-paraphenylene-diamines; ortho-aminophenols, and heterocylic developer compounds, and suitable derivatives of each of these.

A wide variety of primary intermediates can be employed in this invention including, for example, paraphenylenediamines, corresponding to the formula:

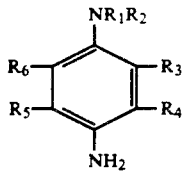

in which:

$R_1$ and $R_2$, which may be identical or different, can denote hydrogen, a $C_1$-$C_6$ lower alkyl group, a $C_1$-$C_6$ alkyl radical substituted with one or more hydroxy group(s) or with a methoxy, methylsulphonylamino or aminocarbonyl group, a furfuryl group, or a phenyl radical optionally substituted with an amino group; $R_3$ and $R_6$ can denote, independently of one another, hydrogen, a $C_1$-$C_6$ lower alkoxy group, or a $C_1$-$C_6$ lower alkyl group substituted with one or more hydroxy group(s); and $R_4$ and $R_5$ denote, independently of one another, hydrogen, a $C_{1-6}$ lower alkoxy group, a $C_{1-6}$ lower alkyl group, or halogen atom such as chlorine, as well as their salts with inorganic or organic acids, N,N'-diphenylalkylenediamines in which the phenyl groups are substituted at the para position with an OH or amino group optionally substituted with a $C_{1-6}$ alkyl group, it being possible for the amino groups joined by the alkylene group to be substituted with $C_{1-6}$ alkyl, $C_1$-$C_6$ hydroxyalkyl or $C_1$-$C_6$ aminoalkyl.

Among the useful compounds of formula (I), there may be mentioned p-phenylenediamine, 2-methyl-paraphenylenediamine, 2-methoxy-para-phenylenediamine, 2-chloro-N-methyl-para-phenylenediamine, N -phenyl-para-phenylenediamine, N-furfuryl-para-phenylenediamine, 3-methoxy-$N^1$-methyl-paraphenylenediamine, 2-chloro-para-phenylenediamine, N-methyl-para-phenylenediamine, 2,3-dimethyl-paraphenylene-diamine, 5-chloro-$N^1$-methyl-p-phenylenediamine, 5-methyl-$N^1$, $N^1$- dimethyl-p-phenylenediamine, 5-methyl-$N^1$-ethyl-N 1- (aminocarbonylmethyl) -p-phenylenediamine, 5-methyl-$N^1$-ethyl-N 1- (methylsulphonylaminoethyl)-p-phenylenediamine, N-(2-methoxyethyl)-p-phenylenediamine, 2,6-dimethyl-p-phenylenediamine, N,N-bis(2-hydroxyethyl)-p phenylenediamine. The N,$N^1$ -diphenylalkylenediamines include, for example N,$N^1$-bis-(2 -hydroxyethyl)-N,$N^1$-bis (p-aminophenyl)ethylenediamine. Their salts with acids such as the monohydrochlorides, dihydrochlorides or sulphates are also suitable.

Among p-aminophenols which are more especially usable according to the invention, there may be mentioned p-aminophenol, 2-methyl-p-aminophenol, 2,3-dimethyl-p-aminophenol, 2,6-dimethyl-p-aminophenol, 3-methoxy-p-aminophenol, 2-chloro-p-aminophenol, 2-hydroxymethyl-p-aminophenol, N-methyl-p-aminophenol and 3-(methylthio)-p-aminophenol, of which p-aminophenol is preferred.

Suitable ortho developers are ortho-aminophenol, 5-chloro-ortho-aminophenol, ortho-phenylenediamine and 3-methyl-ortho-phenylenediamine.

Among heterocyclic developers, it is preferable, according to the invention, to use 2,3-diamino-6-methoxypyridine and 2-(2-hydroxyethyl)amino-5-aminopyridine and their salts, and still more especially, 2-methylamino-3-amino-6-methoxypyridine, 2,5-diaminopyridine, 2-(N-hydroxyethyl)amino-5-amino pyridine, and 2-N,N-bis(2- hydroxyethyl)amino-5-aminopyridine.

More especially preferred oxidation bases are p-phenylenediamine, 2-methyl-p-phenylenediamine, N-(2-methoxyethyl)-p-phenylenediamine, N,N-bis(2-hydroxyethyl)-p-phenylenediamine and p-aminophenol.

Among couplers or colour modifiers, there may be mentioned, in particular, the compounds corresponding to the formula:

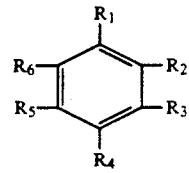

in which:

$R_1$ denotes hydroxy or an amino group which can be substituted with one or more $C_1$-$C_6$ hydroxyalkyl groups; $R_3$ and $R_5$, independently of one another, can denote hydrogen, a hydroxy group, an amino group optionally substituted with a $C_1$-$C_6$ lower hydroxyalkyl group or a $C_1$-$C_6$ lower alkyl group; and $R_2$, $R_4$ and $R_6$ can denote a hydrogen atom or a $C_1$-$C_6$ alkoxy group, a hydroxyalkoxy group or a $C_1$-$C_6$ lower alkyl group; it is also being possible for $R_3$ and $R_4$ together to form a methylenedioxy group.

Among the suitable couplers, there may be mentioned 2-methoxy-5-aminophenol, 2-methoxy-5-[N-(2-hydroxyethyl)amino]phenyl, 1,3-diamino-2,6-dimethoxybenzene, 2-methoxy-1-(N-methylamino)-4- (2-hydroxyethoxy)-3-amino-benzene, 1,3-diamino-6-methoxybenzene, 1,3-diamino-4,6-dimethoxybenzene, 4,6-dimethoxy-1,3-bis[N-(2-hydroxyethyl)-amino]benzene, 2,6-dimethoxy-3-[N-(2-hydroxyethyl]amino]-1-aminobenzene, 2-methyl-5-[N-(2-hydroxyethyl)amino]-phenol, 1,3-bis[N-(2-hydroxyethyl)amino]-4-methoxybenzene, 3-amino-4-methoxyphenol, 3,4-methylenedioxy-1-aminobenzene, 2,6-dimethyl-3-[N-(2-hydroxyethyl)amino]phenol, 2,6-dimethyl-3- aminophenol, 4-ethoxy-1-amino-3-[N,N-bis(2-hydroxyethyl)amino]benzene, (2,4-diaminophenoxy)ethanol, (2-amino-N-methyl-4-aminophenoxy) ethanol, 1-methoxy-2-[N-(2-hydroxyethyl)amino]-4-aminobenzene, 3,4-methylenedioxy-6-ethylphenol, 3,4-methylenedioxy-6-methoxyphenol, 3-amino-6-methoxyaminobenzene, 3-aminophenol, 1,3-dihydroxybenzene-4-(hydroxyethoxy)-1,3-phenylenediamine, 4,6- (dihydroxyethoxy)-1,3-phenylenediamine, and 1,3-phenylenediamine.

Other suitable couplers are 6-aminobenzomorpholine, 1-amino-7-naphthol, 6-hydroxybenzomorpholine, 1-naphthol, 1,3-dihydroxynaphthalene and 1,2-dihydroxy-benzene. Among heterocyclic couplers there may be mentioned 2,6-dihydroxypyridine, 2,6-diaminopyridine, 2-amino-4-hydroxypyridine, 2-hydroxy-4-aminopyridine, 2-hydroxy-5-aminopyridine, 2-amino-6-hydroxypyridine and the like. Included also are further derivatives of 2,6-diamino alkyl pyridines where the amino nitrogen of one or both amino groups is mono- or disubstituted with a $C_1$ to $C_6$ alkyl group such as the methyl, propyl, isopropyl, butyl, iso- or sec-butyl, pentyl, sec-pentyl neopentyl, t-butyl, hexyl, 3-methyl pentyl or 4-methylpentyl groups. The amino groups of either the amino-4-hydroxy- or 2-hydroxy-4-amino-pyridines may also have mono- or di- $C_1$-$C_6$ alkylation on the nitrogen atoms.

The 2,6-amino-, or 4-amino-2-hydroxy- or 2-amino-4-hydroxy pyridine nitrogens may also either singularly or doubly be derivatized with alkoxy substituents of carbon lengths of 1 to 6 with specific mention of 2-hydroxyethyl, 3-hydroxypropyl, 4-hydroxybutyl, 5-hydroxypentyl, 6-hydroxyhexyl, 2-hydroxypropyl, 2-hydroxybutyl, 2-hydroxypentyl, 2-hydroxyphexyl, 3-hydroxybutyl, 3-hydroxypentyl, 3-hydroxyphexyl, 4-hydroxypentyl and 5-hydroxypentyl groups.

Below are listed some of the preferred primary intermediates and couplers for use in this invention.

Primary Intermediates p-phenylenediamine
p-aminophenol
o-aminophenol
N,N-bis(2-hydroxyethyl)p-phenylenediamine
2,5-diaminopyridine
p-toluenediamine Couplers resorcinol
m-aminophenol-naphthol
5-amino-o-cresol
2-methylresorcinol
5-amino-2-(N,N-dimethylaminomethyl)phenol
4,6-di(hydroxyethoxy)-1,3-phenylenediamine Well known conventional additives usually employed in oxidative hair coloring compositions such as thickeners, surface active agents, antioxidants, fragrances and chelating agents may be included in the compositions of the inventions. Such compositions are preferably liquid solutions but they may be in the form of emulsions, suspensions, lotions, or gels.

Surface active agents employed in the dyeing compositions of this invention can be anionic, nonionic or cationic. By way of examples of the various types of surface active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester; myristyl sulfate; glyceryl monostearate; triethanolamine oleate, sodium salt of palmitic methyl taurine; cetyl pyridinium chloride; lauryl sulfonate; myristyl sulfonate; lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; 2-amino-2-methyl propanol; triethanolamine salt of p-dodecylbenzene sulfonate; triethanolamine salt of p-dodecylbenzene sulfonate; nonylnaphthalene sodium sulfonate; dioctyl sodium sulfosuccinate; sodium N-methyl-N-oleoyl taurate; oleic acid ester of sodium isothionate; sodium dodecyl sulfate; the sodium salt of 3-0-diethyl tridecanol-6-sulfate and the like. The quantity of surface active agent can vary over a wide range, such as from about 0.05% to 15% and preferably from about 0.10 to 5% by weight of the composition.

A thickening agent may also be incorporated in the dyeing composition of this invention which may be one or several of those commonly used in hair dyeing. These are exemplified by such products as sodium alginate or gum arabic, or cellulose derivatives, such as methylcellulose, e.g., Methocel 60HG, or the sodium salt of carboxymethylcellulose, or hydroxyethylcellulose, e.g., Cellosize QP-40 or acrylic polymers, such as polyacrylic acid sodium salt, or inorganic thickeners, such as bentonite. The quantity of this thickening agent can also vary over a wide range, even as high as 20%. Ordinarily it will range from 0.5 to 5% by weight of the composition. The viscosity, of the composition may vary from about 1 cp to about 100,000 cps. For a typical lotion formulation, composition viscosity is between about 100 cps to about 10,000 cps.

It may also be useful to incorporate an antioxidant in the present dye compositions. A variety of antioxidants are known in the prior art which would be useful for this purpose. Among these, mention may be made of the inorganic sulfites, e.g., sodium sulfite, thioglycollic acid and other mercaptans, butylated hydroxytoluene, sodium dithionite, various forms of ascorbic acid and its derivatives, e.g., sodium ascorbate, erythorbic acid, ascorbyl palmitate, ascorbyl laurate, etc. The quantity of antioxidant when in use can vary quite a bit. However, this will, in general, be up to about 1%, typically 0.001 to 1% by weight.

The dyeing compositions of this invention are preferably aqueous compositions. The term aqueous composition is used herein in its usual generic sense as embracing any water-containing composition useful for the present purposes. This includes true solutions of the oxidizer, primary intermediates and couplers in an aqueous medium, either alone or in conjunction with other materials, which are also dissolved or dispersed in the aqueous medium. The term aqueous composition also encompasses any mixture of the oxidizer and the dye forming reactants with the aqueous medium either alone or together with other ingredients. The various components may be colloidally dispersed in the medium or may merely be intimately mixed therein. Moreover, the aqueous medium may comprise water or water and additional or auxiliary solvent. Typical auxiliary solvents which may be used to enhance the solubility of the components include ethanol, carbitol, isopropanol, propylene glycol, ethylene glycol, diethylene glycol, diethylene glycol monoethyl ether, glycerine, etc.

The aqueous dyeing compositions of this invention can be prepared by conventional methods used in the hair dyeing art. Thus, they can be prepared by dissolving or suspending the components in the selected media with adequate mixing. Preparation may take place at ambient temperatures, i.e., 20° to 35° C., but solubility and rate of preparation can be enhanced utilizing elevated temperatures, for example 40° to 100° C.

The oxidizer is preferably hydrogen peroxide. It is of importance to note that normal oxidative hair dyeing procedures which employ peroxide gives rise to oxidation of the essential amino acid cystine which is present in the hair. The cystine is oxidized to cysteic acid. This chemical reaction leads to a weakening of the hair structure, making the hair dryer and more prone to breakage. However, we have found that little or no oxidation of cystine occurs at a dyeing pH close to neutral when the metal ions are complexed with dipyridyl or o-phenanthroline in the pretreatment of the present invention.

Because of the different character of its in situ oxidative hair dyeing reactions when pretreating with dipyridyl or o-phenanthroline complexes, the necessary amount of hydrogen peroxide is reduced and in fact will permit the use of less harsh oxidants such as peroxo salts, including for example sodium perborate, percarbonate or even strontium dioxide without slowing the rate of dyeing. When hydrogen peroxide is used, the preferred concentration of as low as 0.1 to 1.0% by weight is effective.

The oxidative dyeing reactions take place rapidly and efficiently while causing less damage than the conventional oxidative dyeing reactions. The damage to hair during the oxidative treatment is well assessed by measuring the amount of cysteic acid formed as a consequence of cystine oxidation. As illustrated in Example 4, cysteic acid formation is quite low in the practice of the present invention, as compared to the prior art processes.

The examples set forth below are given to illustrate the present invention. It will be appreciated that the invention is not limited to these examples which are set forth solely for illustrative purposes. All percentages are by weight.

EXAMPLE 1

The following oxidative dye composition (w) was prepared:

| | |
|---|---|
| paraphenylene diamine | 0.4% |
| 5-amino orthocresol | 0.6% |
| hydrogen peroxide | 3.0% |
| surfactant | 19.0% |
| propylene glycol | 10.0% |
| isopropanol | 3.3% |
| adjuvants | 1.7% |
| monoethanolamine | Q.S. to pH about 6 |
| Water | Q.S. 100% |

The following salt solution (x) was prepared:

| | |
|---|---|
| $CuSO_4$ | 0.006% (Cu II) |
| MEA | Q.S. pH 9.3 |
| water | Q.S. 100% |

The following aqueous solution (y) was also prepared:

| | |
|---|---|
| $CuSO_4$ | 0.006% (Cu II) |
| 2,2'-dipyridyl* | 0.02% |
| sodium hydroxide | to pH 9.3 |
| water | Q.S. 100% |

*Solubilized in ethanol

A second aqueous solution (z) was prepared the same as just above except that o-phenanthroline was substituted for the 2,2'-dipyridyl as a complexing agent. Prior to treatment gray virgin hair was tested for color and intensity using the well known Hunter chromicity values from the Hunter Tristimulus System. The results are reported at entry 1 of Table 1.

A specimen of the same virgin gray hair was treated with the above-described oxidative dye composition (w) for 20 minutes and then tested using the Hunter Tristimulus System. The results are reported at entry 2 of Table 1.

Another specimen of the virgin gray hair was pretreated with the above-described salt solution (x) for 10 minutes, rinsed with water, and followed by a 20 minute oxidative dye (w) treatment. The results of the Hunter Tristimulus System test on the pretreated and dyed hair may be found at entry 3.

Another specimen of the same virgin gray hair was pretreated in the method of the present invention with the aqueous pretreatment composition (y) for 10 minutes, rinsed and oxidatively dyed for 20 minutes with composition (w). The Hunter Tristimulus System results are given at entry 4 of Table 1.

Finally a specimen was pretreated in the manner of the present invention with aqueous solution (z) for 10 minutes, rinsed, and oxidatively dyed with composition (w) for 20 minutes. The Hunter Tristimulus results are reported at entry 5 of Table 1.

The Hunter L value is an indication of color intensity. The lower the L, the darker the color. The value measures greenness or redness of the hairs color. As it increases, the hair has more prominent red, but as it decreases the tonality tends toward greener shades. The b value measures blueness or yellowness. As b increases, the hair tress is more yellow.

Para-phenylenediamine (PPD) and 5-amino-o-cresol (5-AOC) are commonly used dye precursors of oxidation dyeing formulations. The effect of catalysis on hair dyeing with PPD and 5-AOC dye precursors in accordance with the present invention is typical of what would be expected with dye formulations generally. Such formulations often include several primary intermediates and several couplers blended together to obtain the desired color. Depth of color after dyeing would be judged as satisfactory for a Hunter L value of about 15 or less.

For the virgin gray hair dyed without catalyst (entry 2 of Table 1), the Hunter L value was only 23. This inability to provide a satisfactory color is a consequence of the low dye composition (w) pH, the low pH of 6 slowing down the rate of dye formation. If a higher pH were used, the degree of hair damage would, however, be much greater. When the same hair was pretreated with copper II salt under identical conditions, the Hunter value was lowered somewhat, to 19.1. This depth of color is also unsatisfactory.

When the same hair was pretreated with either the Cu-dipyridyl or the Cu-o-phenanthroline complex of the present invention, depth of color was increased significantly, to Hunter L values of 14.0 and 14.5, respectively. It can therefore be seen that the increase in depth of color is attributable to the copper complexes of the present invention by comparison of entries 3, 4 and 5 of Table 1.

TABLE 1

Effect of Various Catalysts on Oxidative (virgin hair) Dyeing at Low pH (Ca 6)

| Entry | Pretreatment | L | a | b | Color |
|---|---|---|---|---|---|
| 1 | — | 35.1 | 0.5 | 7.1 | grey |
| 2 | — | 23.0 | 6.4 | 2.1. | med. grey |
| 3 | Cu-II | 19.1 | 3.0 | 1.7 | red |
| 4 | Cu II/2,2'-Dipyridyl | 14.0 | 2.6 | 1.5 | dk. purple |
| 5 | Cu-II/o-phenanthroline | 14.5 | 2.6 | 1.7 | dk. purple |

EXAMPLE 2

The quantity of copper deposited on gray virgin and non-virgin hair was measured in parts per million (ppm) to ascertain the affinity of the two types of hair for copper; to determine the effect of copper complexation on deposition for the two types of hair, and to determine whether sufficient copper could be deposited from a given solution to reach the threshold catalytic amount.

The results are reported at Table 2.

The "bleached" hair (a) specimens are nonvirgin because they represent gray virgin hair which has been previously bleached with 6% hydrogen peroxide for 20 minutes.

Entries 1 and 2 reflect the disproportionate levels of copper that would be deposited on virgin vs. nonvirgin hair under the process of GILLETTE (German Patent D.E. 2,028,818). This disproportionate affinity would further exaggerate color nonuniformity during subsequent oxidative dyeing of the hair, cause a course hair feel because of an excessive metal content, and result in cystine oxidation.

Entries 3 and 4 show even greater disproportionation if the prior art pretreatment is applied in a shampoo composition.

Entries 5 and 6 show that the pretreatment of the instant invention provides rates of deposition of metal onto virgin and nonvirgin hair sufficient giving rise to substantially uniform rates of subsequent oxidative dyeing. Furthermore, a catalytic amount of metal was possible with a 100-fold decrease in metal concentration solution applied to the hair, even though a slightly longer period of time (10 minutes vs. 5 minutes) was used. The pretreatment did not color the hair.

Entry 7 shows that significantly less copper II is deposited on the virgin hair when the copper sulfate salt is used at a 0.006% level (entry 7) as compared to the deposition obtained with the copper-dipyridyl complex of the present invention (entry 5) under identical treatment conditions.

Entries 8, 9 and 10 show other prior art copper chelate complexes do not reach the threshold catalytic amount of copper deposition at reduced concentrations and short time periods.

Entry 11 shows that shampoo solutions of the Cu-dipyridyl pretreatment on virgin hair after 5 minutes requires more copper applied to the hair to reach the threshold amount than does entry 5 (without shampoo).

TABLE 2

Metal Concentration on Hair After Treatment with Various Catalyst and Potential Catalyst

| Entry | Hair | Treatment | Copper Content ppm |
|---|---|---|---|
| 1 | blended grey | aq. CuSO$_4$, 0.4% Cu, 5 min. | 620 |
| 2 | bleached$^a$ | aq. CuSO$_4$, 0.4% Cu, 5 min. | 1652 |
| 3 | blended grey | shampoo$^b$, 0.5% Cu, 5 min. | 384 |
| 4 | bleached$^a$ | shampoo$^b$, 0.5% Cu, 5 min. | 1219 |
| 5 | blended grey | Cu-Dipyridyl, 0.006% Cu, pH9, 10 min. | 398 |
| 6 | bleached$^a$ | Cu-Dipyridyl, 0.006% Cu, pH9, 10 min. | 512 |
| 7 | blended grey | CuSO$_4$, 0.006% Cu, pH9, 10 min | 26.5 |
| 8 | blended grey | Cu-EDTA, 0.006% Cu, pH9, 10 min. | 32 |
| 9 | blended grey | Cu-Diglym, 0.006% Cu, pH9, 10 min. | 43.2 |
| 10 | bleached$^a$ | Cu-Diglym, 0.006% Cu, pH9, 10 min. | 43.2 |
| 11 | blended | shampoo$^b$, Cu-Dipyridyl, | 138 |
| | grey | 0.03% Cu, 5 min. | |

$^a$blended grey hair treated with 6% H$_2$O$_2$ at pH 9.6 for 20 minutes
$^b$conventional aqueous shampoo composition containing 8.8% surfactant

EXAMPLE 3

The degree of damage to hair occassioned by oxidative dyeing conditions was assessed quantitatively by measuring the concentration of cysteic acid present in the hair before and following treatment. The larger the increase in cysteic acid concentration, the greater the damage to the hair. In these tests dye precursors were omitted because their presence has no significant effect on cysteic acid formation. All tests were conducted on white virgin (Piedmont) hair.

An untreated hair specimen was analyzed for its cysteic acid content in micromoles per gram and that concentration is reported at Entry 1 of Table 3.

A specimen of the same virgin hair was then treated with 3% H$_2$O$_2$ at pH 10 for 30 minutes, which conditions are representative for conventional oxidative dyeing of hair. The cysteic acid content increased significantly as reported at Entry 2 of Table 3.

A specimen of the virgin hair was pretreated in accordance with DE 20 28 818 with 0.1M CuSO$_4$, then bleached with 3% H$_2$O$_2$ at pH 10 for 5 minutes. The results as reported at Entry 3 of Table 3 show that cysteic acid concentration increased considerably as compared to the concentration for the untreated specimen, and was only slightly lower than the concentration reported in Entry 2.

A specimen of the virgin hair was pretreated with the copper II 2,2'-dipyridyl aqueous composition (y) of Example 1, followed by treatment with a 3% H$_2$O$_2$ solution having a pH of 6.5, the cysteic acid concentration being measured after 5 and 20 minutes. The results are reported at Entries 4 and 5. Those results surprisingly indicate that the cysteic acid content is the same as originally measured for the virgin hair prior to any treatment. Entry 6 of Table 3, wherein hair was treated as in entry 2 except at a pH of 6.5, showed significant cysteic acid development at this pH. The amount of cysteic acid developed with regard to the treatment of Entry 5 is significantly less than that developed for the treatment of Entry 6.

TABLE 3

Oxidative Damage on Piedmont Hair

| Entry | Conditions | Cysteic Acid Concentration ($\mu$Mole/g) |
|---|---|---|
| 1 | Untreated | 29.1 |
| 2 | 3% H$_2$O$_2$ pH 10, 30 min. | 83.9 |
| 3 | 0.1M CuSO$_4$ pretreament* 3% H$_2$O$_2$, pH 10, 5 min. | 73.0 |
| 4 | Cu-dipyridyl pretreamtent as in Table 1 3% H$_2$O$_2$, pH 6.5, 5 min. | 26.7 |
| 5 | Cu-dipyridyl pretreamtent as in Table 1 3% H$_2$O$_2$, pH 6.5, 20 min. | 32.4 |
| 6 | 3% H$_2$O$_2$, pH 6.5, 30 min. | 51.6 |

*Per DE 2,028,818 (Gillette).

EXAMPLE 4

The processes of the present invention (Entries 1-6, 8, 10 and 12) were conducted under the pretreatment conditions of the copper II-2,2'-didyridyl used in Example 1 for several oxidative dyeing conditions using a number of different coupler and primary intermediate combinations. Entries 7, 9, 11 and 13 report the results of dyeing without catalyst at otherwise identical conditions, as noted in the footnotes to Table 4. Each of the paired comparisons (6 and 7; 8 and 9; 10 and 11, and 12 and 13) demonstrate that a much greater depth of color (L value) is obtained with the process of the present invention.

TABLE 4

Dyeing With Cu-dipyridyl Catalyst

| Entry | Coupler/Primary Interm. | Dyeing Condition | Hunter Tristimulus L | a | b | Color |
|---|---|---|---|---|---|---|
| 1 | 5-amino-o-cresol/PPD | A | 15.1 | 3.7 | 1.1 | dark purple |
| 2 | 5-amino-o-cresol/PAP | A | 24.2 | 3.1 | 8.6 | orange brown |
| 3 | 1-naphthol/N,N-bis(hydroxyethyl)PPD | A | 19.6 | −1.1 | −5.6 | blue |
| 4 | 3-$NH_2$-6-$CH_2NMe_2$-phenol/N,N-bis(hydroxyethyl)PPD | A | 16.9 | −1.5 | −3.6 | blue |
| 5 | resorcinol/PPD | A | 15.2 | 0.6 | 2.6 | dark grey |
| 6 | 2,4-$(NH_2)_2$-6-(OH)-pyrimidine/PPD | B | 12.3 | 2.9 | −0.9 | black purple |
| 7 | 2,4-$(NH_2)_2$-6-(OH)-pyrimidine/PPD | C | 19.6 | 3.2 | −0.2 | medium red |
| 8 | 2,4-$(NH_2)_2$-6-(OH)-pyrimidine/Cl-PPD | B | 13.8 | 5.4 | 2.4 | dark red |
| 9 | 2,4-$(NH_2)_2$-6-(OH)-pyrimidine/Cl-PPD | C | 22.1 | 4.0 | 2.5 | light red |
| 10 | 2,4-$(NH_2)_2$-6-(OH)-pyrimidine/N,N-bis(hydroxyethyl)PPD | B | 12.6 | 2.2 | −5.4 | blue |
| 11 | 2,4-$(NH_2)_2$-6-(OH)-pyrimidine/N,N-bis(hydroxyethyl)PPD | C | 20.0 | 0.7 | −1.3 | light blue |
| 12 | 5-amino-o-cresol/2,6-$(OH)_2$-4,5$(NH_2)_2$-pyrimidine | D | 16.4 | 7.3 | 3.0 | red |
| 13 | 5-amino-o-cresol/2,6-$(OH)_2$-4,5$(NH_2)_2$-pyrimidine | E | 25.1 | 2.5 | 4.7 | light orange |

Dyeing Conditions:
A coupler 1.2%, prim. int. 0.6%. $H_2O_2$ 3%. 5 min., pH 7, pretreatment (as in Table 1)
B coupler 1%, prim. int. 0.1%. $H_2O_2$ 3%. 20 min, pH 7, pretreatment.
C as B without pretreatment
D coupler 1%, prim. int. 1%. $H_2O_2$ 0.6%, 20 min., pH 7, pretreatment.
E as D. without pretreatment
grey hair (L,a,b.: 35.1.0.5,7.1)

What is claim is:

1. A method for dyeing hair having virgin and nonvirgin hair portions in an oxidative hair dyeing process, comprising:
   (a) contacting the hair with an aqueous solution of a transition metal ion complexed with a chelating agent selected from the group consisting of 2,2'-dipyridyl and o-phenanthroline, present at a concentration sufficient to effect deposition of the complex on the hair, said contact being for a period of time to deposit a noncoloring, catalytically effective amount of said complex on the hair; and
   (b) contacting the catalytically treated hair with an oxidative hair dye mixture comprising dye precursors and an oxidant for a period of from 5 to 30 minutes, whereby the time to produce a desired shade of color in the hair is substantially reduced and the color imparted to the virgin and nonvirgin hair portions is substantially uniform.

2. The method of claim 1 wherein the transition metal is copper-II.

3. The method of claim 1 wherein the amount of metal deposited onto the hair is from about 100 to about 1000 ppm.

4. The method of claim 2 wherein the amount of copper deposited on the hair is from about 100 to about 1000 ppm.

5. The method of claim 1 wherein the concentration of metal/chelate complex in aqueous solution required to effect a catalytic effective deposition onto the hair is from about 0.001 to about 0.1% by weight of the solution.

6. The method of claim 5 wherein the transition metal is copper II.

7. The method of claim 6 wherein the concentration is about 0.01%.

8. The method of claim 1 wherein step (b) is conducted at a pH of about 6 to about 8.5.

9. The method of claim 1 wherein the oxidant is hydrogen peroxide.

10. The method of claim 9 wherein the concentration of hydrogen peroxide may be as low as 0.1%.

11. The method of claim 1 wherein the period for contacting the hair with the oxidative hair dye composition is from 5.0 to 15.0 minutes.

12. The method of claim 1 wherein only virgin hair is treated.

* * * * *